United States Patent [19]

Tomoff

[11] 4,312,591
[45] Jan. 26, 1982

[54] APPARATUS FOR AUTOMATICALLY TRANSPORTING LIQUID SAMPLES TO AN ANALYZER

[75] Inventor: Toma Tomoff, Uberlingen, Fed. Rep. of Germany

[73] Assignee: Bodenseewerk Perkin-Elmer & Co. GmbH, Fed. Rep. of Germany

[21] Appl. No.: 56,751

[22] Filed: Jul. 12, 1979

Related U.S. Application Data

[63] Continuation of Ser. No. 8,226, Jan. 31, 1979, abandoned.

[30] Foreign Application Priority Data

Jul. 2, 1978 [DE] Fed. Rep. of Germany ....... 2805137

[51] Int. Cl.³ .......................................... G01N 21/73
[52] U.S. Cl. .................................. 356/315; 356/246; 356/417
[58] Field of Search ................................ 356/315, 417

[56] References Cited

U.S. PATENT DOCUMENTS 3,163,699 12/1964 Staunton ............................. 356/315
3,740,157 6/1973 Kasparek ............................ 356/246

FOREIGN PATENT DOCUMENTS 263962 1/1927 United Kingdom .
368214 3/1932 United Kingdom .
857900 1/1961 United Kingdom .
1014462 12/1965 United Kingdom .
1029989 5/1966 United Kingdom .
1245241 9/1971 United Kingdom .
1337800 11/1972 United Kingdom .
1465002 2/1977 United Kingdom .
1465678 2/1977 United Kingdom .
1503731 3/1978 United Kingdom .

Primary Examiner—Vincent P. McGraw
Attorney, Agent, or Firm—S. A. Giarratana; F. L. Masselle; R. A. Hays

[57] ABSTRACT

Disclosed is apparatus for automatically transporting liquid samples from sample vessels to the burner of a flame atomic absorption spectrometer or a flame photometer. A sample feed tube pivots between a first position with its end disposed in a sample feeding vessel for discharging, in sequence, sample liquid and a flushing liquid into the feeding vessel and a second position with its end in communication with a sample vessel. The sample feeding vessel has an upper opening, a bottom outlet, and a cavity between the outlet and opening having an annular convex interior surface to ensure accurate and repeated insertion of the sample feed tube into the sample feeding vessel when the sample feed tube is moved into its first position and full and complete discharge of the sample liquid into the sample feeding vessel. A control mechanism is provided to prevent discharge of the sample liquid from the sample feed tube unless and until the sample feed tube obtains its first position.

13 Claims, 4 Drawing Figures

APPARATUS FOR AUTOMATICALLY TRANSPORTING LIQUID SAMPLES TO AN ANALYZER

BACKGROUND OF THE INVENTION

This application is a continuation of U.S. patent application Ser. No. 008,226 filed Jan. 31, 1979, now abandoned.

In flame atomic absorption spectrometers or in flame photometers, a burner having an elongated gas outlet slot is normally provided. A fuel-gas air mixture is supplied to the slot and an elongated flame is thus provided by the burner. This flame is traversed in a longitudinal direction by the measuring beam of the spectrometer. An atomizer is provided and forms a mist consisting of finely distributed droplets of the liquid sample. This mist is sprayed into the fuel-gas air mixture. The sample liquid is accordingly atomized in the flame, and the atoms of the element under investigation cause measurable attenuation of the measuring beam.

Usually continuous atomization occurs, i.e. sample liquid is supplied to the atomizer for the full duration of the measurement, and a stationary measuring signal is generated. This however, involves certain problems. First, a rather large quantity of sample liquid is required to generate a measuring signal of a certain amplitude. Often the sample contains components which deposit as a crust on the burner opening. This alters the geometry of the burner opening. Furthermore, interfering signals may be generated with consecutive analyses. Thus, the crust must be frequently removed and this, undesirably, involves considerable work, particularly because the instrument must be subsequently re-adjusted and recalibrated.

To avoid these disadvantages, it is known to supply metered, rather small, quantities of the sample to the measuring instrument by means of a pipette through a sample feeding vessel connected to the atomizer. Each of the samples thus supplied will generate a peak, the height of which represents a measure of the quantity of the investigated substance in the sample. Because only small sample quantities are supplied with each run, which is advantageous per se, the risk of forming a crust on the burner is also considerably reduced (See E. Sebastiani, K. Ohls and G. Riemer "Ergebnisse zur Zerstaubung dosierter Losungsvolumina bei der AAS" Z. Anal. Chem 264, 105–109 (1973)).

Furthermore, it is known to automate the supply of metered solution volumes in atomic absorption spectroscopy. (See Berndt and E. Jackwerth "Automated Injection Method for Dispensing Small Volume Samples in Flame Atomic Absorption" in "Atomic Absorption Newsletter" Vol. 15.109–112 (1976) and also U.S. Pat. No. 4,068,529 issued Jan. 17, 1978 of common assignee herewith.) With this prior art arrangement, a device is used which is normally utilized for feeding samples to a graphite tube atomizer in flameless atomic absorption spectroscopy. Particularly, a sample feed tube movable between a sample vessel and the filler opening of a graphite tube atomizer is provided. Sample liquid is suctioned into the sample feed tube by a sample pump. After swinging movement of the sample feed tube, the sample liquid is then dispensed into the graphite tube of the graphite tube atomizer. The sample feed tube is then flushed by a flushing liquid, which is supplied by means of a flushing liquid pump coupled to the sample feed tube for flow through the sample feed tube and into a waste vessel.

With serial analyses, it is essential to avoid cross-contamination of samples. Should remnants of a previously analysed sample remain, the results of the subsequent sample analyses will not be accurate. In flameless atomic absorption spectroscopy using a graphite tube, the graphite tube is heated out between individual analyses, whereby sample remnants are vaporized and driven out by inert gas flow. In devices for supplying samples to the burner of flame atomic absorption spectrometers or flame photometers, however, cross-contamination may be caused by sample remnants remaining in the atomizer or in the sample feeding vessel. The sample feeding vessel, of course, receives the metered sample liquid volume from the sample feed tube and is connected to the atomizer through a hose. It has been suggested to flush the system between analyses. This, however, presents many problems. First, the quantity of flushing liquid which can be supplied to the sample feeding vessel between analyses is limited, as the next analysis can start only after the entirety of the flushing liquid has been suctioned into the atomizer and sprayed into the flame. Therefore, large quantities of flushing liquid would undesirably extend the time intervals between individual analyses. The flushing liquid level in the sample feeding vessel must, however, be sufficient such that all parts of the sample feed tube having prior contact with the sample liquid are cleansed by the flushing liquid. These countervailing factors could be accommodated by providing a correspondingly small diameter in the sample feeding vessel. However, this presents problems in guiding the sample feed tube accurately enough so that it can be properly inserted into the sample feeding vessel.

SUMMARY OF THE INVENTION

Accordingly, it is a primary object of the present invention to provide an apparatus for automatically transporting liquid samples from sample vessels to the burner of a flame atomic absorption spectrometer or a flame photometer having a sample feed tube for feeding sample liquid into a sample feeding vessel wherein proper, accurate, insertion of the sample feed tube into the sample feeding vessel and complete discharge of the sample liquid from the sample feed tube into the sample feeding vessel are ensured.

To accomplish the foregoing objects as well as other objects and advantages, the present invention provides a sample feeding vessel having a funnel-shaped cavity with an inner surface which, in longitudinal section, is convex to the inside. This presents a small volume with a relatively large upper opening for ensuring accurate and repeatable disposition of the sample feed tube in the opening upon its movement from the sample vessel to the sample feeding vessel. Also, by engaging the tip of the flexible feed tube against the inner surface of the sample feeding vessel, complete discharge of the sample liquid from the sample feed tube into the sample feeding vessel is ensured.

An additional object of the present invention is to provide apparatus for automatically transporting liquid samples from sample vessels to the burner of a flame atomic absorption spectrometer or a flame photometer having a sample feed tube for feeding sample liquid into a sample feeding vessel wherein the sample feeding vessel is flushed by a flushing liquid after each analysis, the flushing liquid being supplied conveniently, and in a small quantity.

To accomplish this objective, a flushing liquid pump for feeding flushing liquid in one direction only from a flushing liquid container is coupled to the sample feed tube. A program control device controls this operation of the flushing liquid pump such that a quantity of flushing liquid is pumped into the sample feeding vessel to substantially fill the vessel after the sample liquid has been dispensed from the sample feeding vessel. Thus, the sample feeding vessel is flushed with a flushing liquid after each analysis.

With devices of this type, it is also necessary to synchronize the dispensing of the sample liquids, which may be acid or corrosive solutions, with the insertion of the sample feed tube into the sample feeding vessel to ensure that the sample liquid cannot be splashed beside the sample feeding vessel, for example, should the mechanism moving the sample feed tube jam. In accordance with another aspect of the present invention, the program control device hereof precludes this and comprises a pump motor arranged to actuate the sample pump to dispense the sample liquid only when the intake and discharge end of the sample feed tube lies in the sample feeding vessel.

In one aspect hereof, the present invention provides new and improved apparatus for automatically transporting liquid samples from sample vessels to the burner of a flame atomic absorption spectrometer or a flame photometer, comprising: a sample feed tube having an intake and dispensing end; sample pump means coupled to the sample feed tube for taking in and dispensing a predetermined volume of a sample liquid through the intake and dispensing end of the sample feed tube; a sample feeding vessel for receiving the sample liquid from the sample feed tube and communicating the sample liquid to the burner of the spectrometer or photometer; means for moving the sample feed tube between a first position with the intake and dispensing end thereof in communication with the sample feeding vessel and a second position in communication with a sample vessel; pump means coupled to the sample feed tube for pumping a flushing liquid through the sample feed tube into the sample feeding vessel when the sample feed tube lies in its first position; and control means coupled to the sample pump means, the flushing liquid pump means and the moving means for, in sequence, taking in a predetermined volume of sample liquid from the sample vessel when the sample feed tube lies in the second position, moving the feed tube from its second position to its first position, dispensing the sample liquid from the feed tube into the sample feeding vessel for discharge into the burner, and pumping flushing liquid through the feed tube into the sample feeding vessel.

In another aspect hereof, the present invention provides new and improved apparatus for automatically transporting liquid samples from sample vessels to the burner of a flame atomic absorption spectrometer or a flame photometer, comprising: a sample feeding vessel having an opening at an upper end thereof for receiving sample liquid and an outlet at its lower end for communicating the sample liquid to the burner of the spectrometer or photometer, the sample feeding vessel having an interior cavity in communication with the opening and outlet and defined, at least in part, by a substantially annular convex surface; a sample feed tube for discharging sample liquid through an end thereof into the sample feeding vessel; means for moving the sample feed tube between a first position with the end thereof in communication with the sample feeding vessel and a second position in communication with a sample vessel; and pump means coupled to the sample feed tube for discharging sample liquid from the sample feed tube into the sample feeding vessel when the sample feed tube lies in its first position, the sample feed tube end in its first position lying in contact with the surface of the sample feeding vessel to ensure complete discharge of the sample liquid from the end of the sample feed tube.

In still a further aspect hereof, the present invention provides new and improved apparatus for automatically transporting liquid samples from sample vessels to the burner of a flame atomic absorption spectrometer or a flame photometer, comprising; a sample feeding vessel for receiving the sample liquid and communicating the sample liquid to the burner of the spectrometer or photometer, a sample feed tube for transporting sample liquid from the sample vessels to the sample feeding vessel; means for moving the sample feed tube between a first position with its end in communication with the sample feeding vessel and a second position in communication with a sample vessel; pump means coupled to the sample feed tube for taking in sample liquid from a sample vessel when the sample tube lies in its second position and for discharging sample liquid from the sample feed tube into the sample feeding vessel when the sample feed tube lies in its first position; and control means coupled to the pump means and the moving means for disabling the pump means from discharging sample liquid from the sample feed tube when the sample feed tube lies intermediate its first and second positions and responsive to movement of the sample feed tube into its first position to enable the pump means to discharge sample liquid into the sample feeding vessel.

The foregoing and other objects and advantages of the present invention will be best understood by reference to the following detailed description of a preferred embodiment of the invention, the appended claims and attached drawings.

DETAILED DESCRIPTION OF A PREFERRED EMBODIMENT OF THE PRESENT INVENTION

Figure 1:
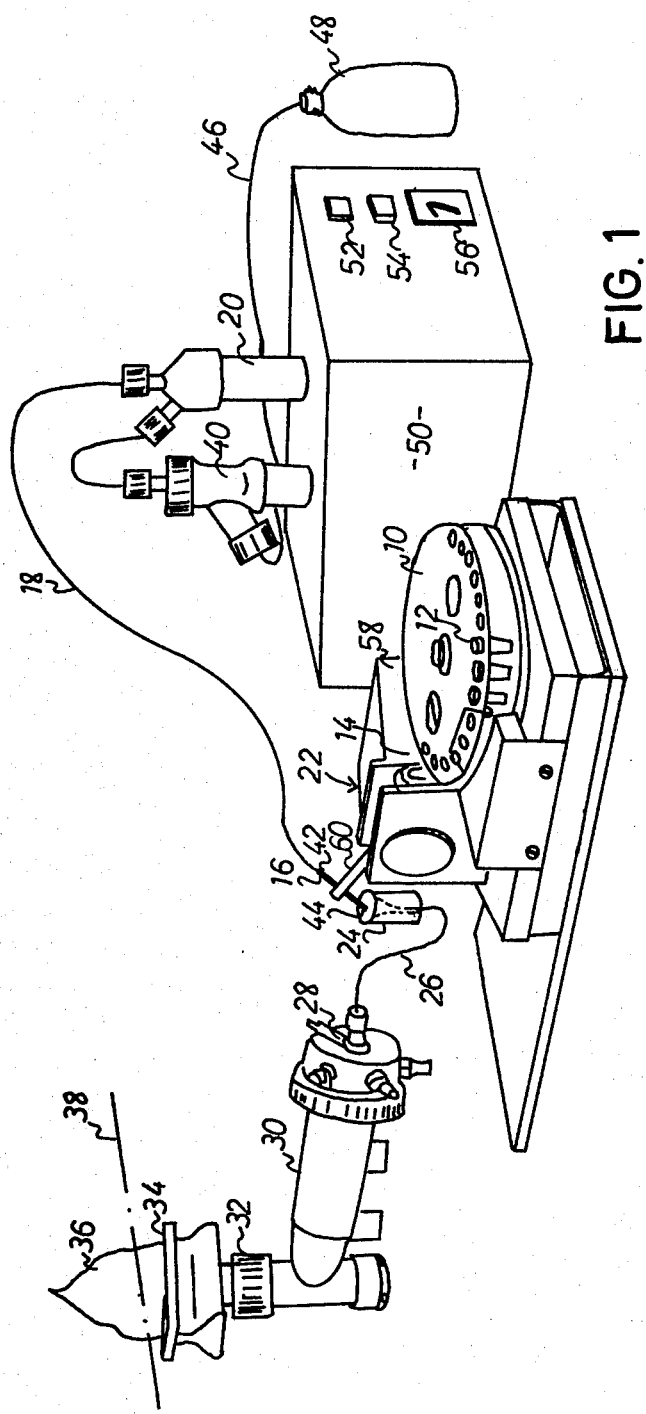
FIG. 1 is a schematic-perspective illustration of an apparatus for transporting liquid samples to the burner of an atomic absorption spectrometer.

Referring to the drawings in detail, there is illustrated in FIG. 1 apparatus for automatically transporting liquid samples from sample vessels to the burner of a flame atomic absorption spectrometer or a flame photometer constructed in accordance with the present invention and shown in conjunction with the burner of an atomic absorption spectrometer and a turntable for the liquid samples. Specifically, the liquid samples are arranged on a turntable 10 in sample vessels 12. Turntable 10 is mounted on a base for stepwise rotary movement so that each sample vessel is rotated in succession into an operative position denoted 14. In the operative position, a well-defined quantity of sample liquid is suctioned from each sample 12 by means of a sample feed tube 16, which is connected to a sample pump 20 through a hose 18. Sample feed tube 16 is pivotally mounted for movement by a mechanism 22 between a first position illustrated in FIG. 1 in which feed tube 16 lies in communication with a feeding vessel 24 and a second position in communication with a sample vessel 12. In the first position of feed tube 16, sample pump 20 makes its discharge stroke so that sample liquid previously suctioned into feed tube 16 from sample vessel 12 is dispensed into sample feeding vessel 24. A conduit 26 extends from the bottom of sample feeding vessel 24 and the sample liquid deposited in vessel 24 is suctioned through conduit 26 by an atomizer 28. Atomizer 28 sprays the sample liquid as a fine mist into a fuel-gas air mixture in a mixing chamber 30. This fuel-gas air mixture, together with the finely distributed sample liquid mist, is then supplied to a burner 32 having an elongated burner opening 34. An elongated flame 36 burns in burner opening 34 and is traversed by the measuring beam 38 of an atomic absorption spectrometer. By supplying a well-defined discrete quantity of sample liquid to sample feeding vessel 24 and atomizing the sample liquid in the fuel-gas air mixture, the atomic absorption spectrometer will provide a signal peak the height of which represents a measure of the quantity of a looked-for element, i.e., the element under investigation in the sample liquid.

After this measurement has been carried out, a mastered quantity of a flushing liquid is dispensed into sample feeding vessel 24 by a flushing pump 40, which is also connected to sample feed tube 16 through hose 18. The quantity of flushing liquid dispensed is determined such that the sample feeding vessel 24 is substantially completely filled with flushing liquid, and such that all parts at the intake and dispensing end 44 of the sample feed tube 16 which contacted the sample liquid are washed by the flushing liquid. Subsequently, the flushing liquid is suctioned into atomizer 30 through hose 26 thus flushing hose 26 and atomizer 30 to reduce the risk of crosscontamination. Flushing pump 40 feeds in one direction only and suctions the flushing liquid through a hose 46 from a flushing liquid container 48.

Subsequent to the flushing procedure, sample feed tube 16 is pivoted and returned to its second position by mechanism 22, for communication with a sample vessel 12 which is then in its operative position 14. This sample vessel 12 may be the same sample vessel used in the preceding analysis if multiple analysis of a single sample is programmed. Alternatively, turntable 10 may advance a single step prior to return of feed tube 16 to its second position.

Figure 2:
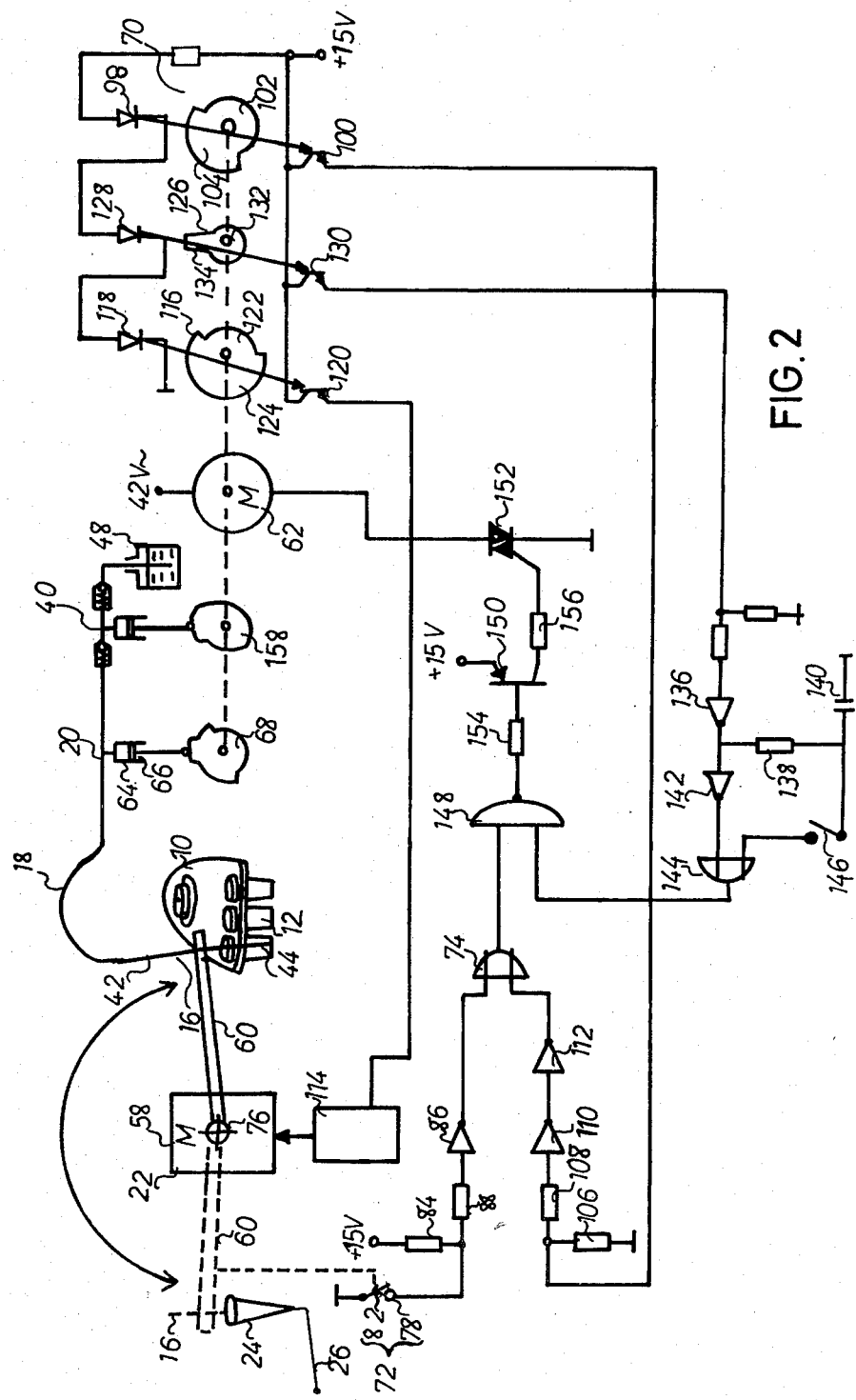
FIG. 2 is a schematic illustration of a program control device for use with the apparatus hereof.

A program control device 50, illustrated in FIG. 2, is provided to control the foregoing and other movements as will be apparent from the ensuing description. Program control device 50 has a switch-on button 52 and a start-stop button 54. In addition, the number of the analysis to be carried out with each sample can be selected by a setting device 56.

Referring now to FIG. 2, mechanism 22 comprises a servomotor 58 with a gear, not shown, arranged to rotate a pivot arm 60 (FIGS. 1 & 2) carrying sample feed tube 16. Servomotor 58 is designed to brake to rest with an applied voltage and is therefore able to operate against fixed stops. Two positions of servomotor 58 are defined by two stops. In a first position of servomotor 58, sample feed tube 16 is positioned with its intake and dispensing end 44 in sample feeding vessel 24 as illustrated by the dashed lines representing feed tube 16 in FIG. 2. In a second position of servomotor 58, the sample feeding tube is positioned with its intake and dispensing end 44 in sample vessel 12 located in its operative position 14, as illustrated by the full line position of feed tube 16 in FIG. 2.

Program control device 50 comprises a pump motor 62 which drives sample pump 20 through a cam 68. Sample pump 20 comprises a cylinder 64 and a piston 66 for suctioning hose 18 to draw sample liquid into feed tube 16 on the intake stroke of pump 20 and pressurizing hose 18 for discharging sample from feed tube 16 on the power stroke of pump 20. Cam 68 has a cam surface acting on a roller connected to a piston 66 in cylinder 64 of pump 20. Piston 66 is thus movable to discharge sample liquid in response to a predetermined operative discharge angular range of rotary movement of cam 68 and also pump 62. Piston 66 is thus also movable to suction sample liquid in response to a predetermined operative intake angular range of rotary movement of cam 68 and also of pump motor 62.

The program control device 50 also includes a sensor 70 which responds to movement of pump motor 62 and provides signals "0" and "L" respectively within different operative ranges of the cam 68 and cam 158. An "0" signal means logic zero and an "L" signal means logic one. Furthermore, a second sensor 72 is provided which responds to the movement of mechanism 22 and provides a signal "L" only when the servomotor 58 is in its first position, e.g., the sample feeding tube 16 is positioned with its intake and dispensing end 44 within sample feeding vessel 24. Pump motor 62 is energized by signals from the first and second sensors 70 and 72, respectively through an OR logic circuit with an OR gate 74.

Figure 3:
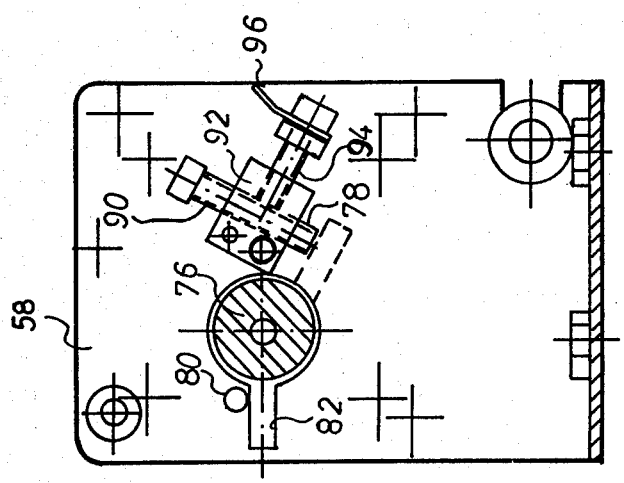
FIG. 3 is an enlarged end elevational view of a servomotor for use with the present invention with parts in cross section and further illustrating a sensor responsive to the movement of the servomotor.

Mechanism 22 includes a pivot arm 60 carrying sample feed tube 16 and which arm 60 is fixed to shaft 76 of electric servomotor 58. Shaft 76 is movable between two stops 78 and 80, respectively, determining the first and second positions respectively of arm 60. One of the stops 78, which is associated with the first position of servomotor 58, constitutes a switch contact and forms part of said second sensor 72. A limiting pin 82 (FIG. 3) is fixed to shaft 76 and is, in turn, electrically connected to ground. Stop 78 associated with the first position of servomotor 58 is insulated and is connected through a resistor 84 to a voltage, for example 15 volts, representing the signal "L".

Second sensor 72 includes an inverter 86, the input terminal of which is connected to stop 78 through a resistor 88. Its output represents the output signal of second sensor 72. Stop 78 constitutes a screw 90 which is mounted in a block 92 formed of insulating material. A contact screw 94, which is guided in insulating block 92 and carries a soldering lug 96, engages screw 90.

First sensor 70 includes a light chopping device including a light source 98 for generating a light beam, a photoelectric detector 100 in the form of a phototransistor, and a light stop disc 102 rotatable with pump motor 62 and having an edge 104 projecting from part of its periphery into the light beam between light source 98 and detector 100. The output signal of photoelectric detector 100 drops across a resistor 106. The signal picked off resistor 106 is applied through a resistor 108 to an inverter 110, the output signal of which is once more inverted by a further inverter 112. The output signal of inverter 112 represents the output signal of first sensor 70, which together with the output signal of the second sensor 72, is applied to OR gate 74.

Servomotor 58 is arranged to be reversed by a third sensor 116 through a switch 114. Third sensor 116 responds to the movement of pump motor 62 and causes energization of servomotor 58 for rotation towards its first position, i.e., counterclockwise as illustrated in FIG. 2, after pump motor 62 has passed through its operative angular range corresponding to the intake stroke of the sample pump. Third sensor 116 also causes energization of servomotor 58 for rotation, i.e., in a clockwise direction as illustrated in FIG. 2, towards its second position, after pump motor 62 has passed completely through its operative range completing the discharge stroke of sample pump 20. Third sensor 116 comprises a light chopping device including a light source 118 for generating a light beam, a photoelectric detector 120 in the form of a phototransistor, and a light stop disc 122 rotatable with pump motor 62 and having an edge 124 projecting from part of its periphery into the light beam between light source 118 and detector 120.

In addition, a fourth sensor 126 is provided which comprises a light chopping device including a light source 128 for generating a light beam, a photoelectric detector 130, and a light stop disc 132 rotatable with pump motor 62. Peripheral projection 134 carried by disc 132 extends into the light beam between light source 128 and detector 130 when pump motor 62 is in a rest position. The output signal of sensor 126, which has the value "L" when the light beam is uninterrupted, is inverted by a first inverter 136, applied to an RC filter including a resistor 138 and a capacitor 140, and, in addition, is once again inverted by a second inverter 142. This latter signal is applied to the input terminal of OR-gate 144 through a START contact switch 146. The output of the OR-gate 144 is applied to one input of an AND-gate 148. Signals from the first and second sensors 70 and 72 respectively logically combined by the OR-gate 74, are applied to the other input terminal of AND-gate 148. The output terminal of AND-gate 148 is arranged to energize pump motor 62 through a transistor 150 and a triac 152. To this end, the output terminal of AND-gate 148 is connected to the base of transistor 150 through a resistor 154. The emitter of transistor 154 is connected to a supply voltage, e.g. 15 volts, and its collector is connected to the control electrode of triac 152 through a resistor 156.

A pump is provided for supplying flushing liquid to sample feeding vessel 28. Pump 40 feeds flushing liquid in one direction from a flushing liquid container 48 and is coupled to the rear end 42 of sample feed tube 16. This flushing liquid pump 40 is actuated by a cam 158 rotated by pump motor 62. Flushing liquid is dispensed through feed tube 16 within the operative discharge range of pump motor 62 and after sample liquid has been dispensed through feed tube 16, the flushing liquid being dispensed when servomotor 58 and arm 60 lie in their first positions.

Figure 4:
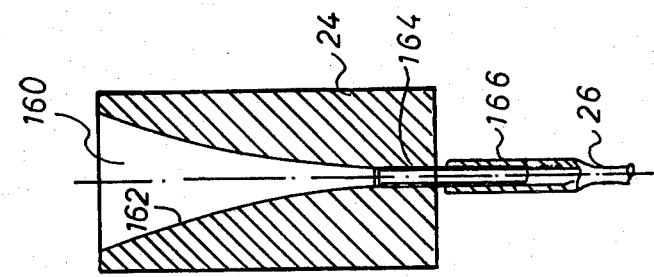
FIG. 4 is an enlarged vertical cross sectional view of a sample feeding vessel constructed in accordance with the present invention.

As best illustrated in FIG. 4, sample feeding vessel 24 has a funnel-shaped cavity 160 with an interior surface 162, which in longitudinal section, is convex to the inside. The generatrix of the inner surface 162 of sample feeding vessel 24 can be represented approximately by an exponential function.

At its lower end, sample feeding vessel 24 terminates in an outlet passage 164 having a cylindrical inner surface. A straight piece of tube 166 is removably received in the outlet passage 164 and extends from sample feeding vessel 24 at its bottom. A hose 26 is disposed about tube 116 and is coupled to atomizer 28. Sample feeding vessel 24 has a non-wettable inner surface 162 and preferably, is formed of a polytetrafluoroethylene material. Sample feed tube 16 consists of a tube formed of a resiliently-flexible material which has a non-wettable surface and may, also for example, be formed of polytetrafluoroethylene.

In operation, pivot arm 60 lies initially in its left hand or first position illustrated by the dashed lines in FIG. 2. This corresponds to the first position of servomotor 58 in which sample feed tube 16 is positioned with its intake and dispensing end 44 in sample feeding vessel 24. The shape of the inner surface 162 of sample feeding vessel 24 ensures that the intake and dispensing end 44 of the tube 16 is accurately inserted into the sample feeding vessel 24. That is, because of the resilient-flexible construction of sample feed tube 16 and the shaping of the interior of sample feeding vessel 24, intake and dispensing and 44 of feed tube 16 is accurately and repeatedly disposable in sample feeding vessel 24. Also and importantly, the volume of cavity 160 in sample feeding vessel 24 is not unduly large, as the diameter of cavity 160 is progressively reduced towards its bottom. When arm 60 lies in its first position, sample feed tube 16 thus resiliently engages the inner surface 162 of the sample feeding vessel 24. This engagement ensures that the entirety of the sample liquid actually leaves sample feed tube 16 for gravity flow along the inner surface 162 of vessel 24. If sample feed tube 16 with its non-wettable surface extended freely into cavity 160 of vessel 24 and did not engage the inner surface 162, drops could be formed at the intake and dispensing end 44 of feed tube 16 and which drops would not be discharged from tube 16 or flow into sample feeding vessel 24 for suction by atomizer 28.

With sample feed tube 16 in its first position, pump motor 62 is energized and passes through its operative range. That is, motor 62 drives cam 68 causing sample pump 20 to make its discharge stroke. This causes feed tube 16 to discharge the sample liquid carried by the tube 16 into sample feeding vessel 14. Pump motor 62 also drives cam 158 which subsequently causes flushing liquid pump 40 to pump flushing liquid carried by the tube 16 into sample feeding vessel 24.

After flushing is completed, switch 114 is actuated by sensor 116 and servomotor 58 is reversed. Pivot arm 60 is thus rotated clockwise, as viewed in FIG. 2, into its second position and sample feed tube 116 is thus immersed into a sample vessel in its operative position 14. Pump motor 62 remains engaged and continues to drive cam 68 causing sample pump 20 to make its intake stroke by which a predetermined volume of sample liquid is suctioned from sample vessel 12 into sample feed tube 16. Pump motor 62 also drives cam 158 causing flushing liquid pump 40 to suction a discrete volume of flushing liquid from container 48. After this procedure is complete, servomotor 58 is again reversed by sensor 116, and pivot arm 60 is again rotated into its first position, illustrated by the dashed lines in FIG. 2. After this position has been obtained, the discrete volumes of sample liquid and flushing liquid are dispensed in sequence into sample feeding vessel 24.

In order to ensure that the sample and flushing liquids are dispensed through sample feeding tube 16 only when the intake and dispensing end 44 of feed tube 16 is located within sample feeding vessel 24, pump motor 62 is energized by sensor 70 and 72 through OR-gate 74. When pump motor 62 has rotated sufficiently such that the intake strokes of pumps 20 and 40 have been completed, edge 104 of disc 102 interrupts the light beam between light source 98 and detector 100. The signal from sensor 70 thus becomes "0". Pump motor 62 is then de-energized and remains at rest, until contacts 82, 78 are closed. These contacts 82, 78 are closed only when servomotor 58 has rotated pivot arm 60 into its end stop or first position with the end 44 of sample feed tube 16 disposed in the sample feeding vessel. When contacts 82, 78 are closed, a signal is applied to OR-gate 74 to energize pump motor 62 and, in sequence, pumps 20 and 40 to respectively discharge sample liquid and flushing liquid. Thus, sample liquid cannot be dispensed from sample feed tube 16, if, for example, the mechanism jams and pivot arm 60 is retained, for one reason or other, in a position intermediate its first and second positions. Conversely, pivot arm 60 will not be returned to its second position by reversing servomotor 58, unless and until the operative discharge range of pump motor 62 has been completed and sample pump 20 and flushing liquid pump 40 have completed their discharge strokes.

Pump motor 62 has a rest position which corresponds to the beginning of a cycle of operation. In this rest position, projection 134 interrupts the light beam between light source 128 and photoelectric detector 130. Sensor 126 thus provides an output signal "0". When start contact 146 is open, OR-gate 144 provides an output signal "0" which is applied to an input-terminal of AND-gate 148. Thus, pump motor 162 is stopped independently of the signals from sensors 70 and 72.

A new cycle is initiated by closing start contact 146. When the light beam between source 128 and detector 130 is interrupted, it provides the output signal "0". In that event, the output signal from inverter 136 will be "L" i.e. the capacitor of the RC-filter is charged with a voltage of 15 volts. Upon closing start button 146, this voltage is applied to OR-gate 144 which in turn, opens AND-gate 148 for signals from sensors 70, 72 and enables motor 62 to start. When motor 62 is started, projection 134 is moved out of the light beam between source 128 and detector 130 and the second input terminal of the OR-gate 144 receives the signal "L". Pump motor 62 then makes one complete revolution, which may be interrupted due to sensors 70, 72 until projection 134 again interrupts the light beam between source 128 and detector 130 to de-energize pump motor 62.

During return movement of sample feed tube 16 to sample vessel 12, sample pump 20 provides a small stroke suctioning a small air volume into hose 18. This separates the flushing liquid contained in hose 18 from the sample liquid subsequently suctioned from sample vessel 12.

Thus, novel and improved apparatus for the transport of liquid samples from sample vessels to the burner of an atomic absorption spectrometer or a flame photometer has been described and illustrated. Although a specific embodiment of the present invention has been described and illustrated, it will be understood that various modifications in the form and detail of the described and illustrated invention may be made without departing from the spirit and scope of the invention. Therefore, the present disclosure should be construed as illustrative rather than limiting.

What is claimed is:

1. Apparatus for automatically transporting liquid samples from sample vessels to the burner of a flame atomic absorption spectrometer or a flame photometer, comprising:
   a sample feed tube having an intake and dispensing end;
   sample pump means coupled to said sample feed tube for taking in and dispensing a predetermined volume of a sample liquid through said intake and dispensing end of said sample feed tube;
   a sample feeding vessel for receiving said sample liquid from said sample feed tube and communicating said sample liquid to said burner, said sample feeding vessel having an opening at an upper end thereof, an outlet at a lower end thereof, and an interior cavity in communication with said opening and said outlet, said cavity being substantially defined by a substantially annular convex surface;
   means for moving said liquid sample feed tube between a first position with said intake and dispensing end thereof in communication with said sample feeding vessel and a second position in communication with a sample vessel;
   pump means coupled to said sample feed tube for pumping a flushing liquid through said sample feed tube into said sample feeding vessel when said sample feed tube lies in said first position; and
   control means coupled to said sample pump means, said flushing liquid pump means and said moving means for, in sequence, taking in a predetermined volume of sample liquid from the sample vessel when said feed tube lies in said second position, moving said feed tube from said second position to said first position, dispensing said sample liquid from said feed tube into said sample feeding vessel for discharge into said burner, and pumping flushing liquid through said feed tube into said sample feeding vessel.

2. Apparatus according to claim 1 wherein said convex surface of said sample feeding vessel being formed of a non-wettable surface.

3. Apparatus according to claim 2 wherein said material of said convex surface comprises polytetrafluoroethylene.

4. Apparatus according to claim 1 wherein said sample feed tube comprises a tube formed of resilient, flexible material.

5. Apparatus according to claim 1 wherein said tube has a surface in contact with said convex surface of said sample feeding vessel when said sample feed tube lies in said first position, the contact surface of said tube being formed of a non-wettable material.

6. Apparatus according to claim 5 wherein said material of said contact surface comprises polytetrafluoroetheylene.

7. Apparatus according to claim 1 wherein said the generatrix of said substantially annular convex surface being represented, at least approximately, by an exponential function.

8. Apparatus according to claim 7 wherein said convex surface of said sample feeding vessel terminates, at its lower end, in an outlet passage having a cylindrical inner surface.

9. Apparatus according to claim 8 including a tube extending from said sample feeding vessel at said outlet thereof, said tube being removably inserted into said outlet, and a hose receivable about said tube providing for communication between said cavity and the atomizer.

10. Apparatus as claimed in claim 1 wherein said control means includes means for disabling said sample pump means from discharging sample liquid from said sample feed tube when said sample feed tube lies in positions intermediate said first and second positions thereof and responsive to movement of said sample feed tube into said first position to enable said sample pump means to discharge sample liquid into said sample feeding vessel.

11. Apparatus according to claim 10 wherein said control means includes a motor coupled to said pump means for actuating, within a predetermined operating range of said motor, said pump means to discharge sample liquid from said feed tube in its first position into said sample feeding vessel, a first sensor, means coupled to said first sensor and responsive to actuation of said pump means within said predetermined operating range thereof to establish a first signal from said first sensor and responsive to actuation of said pump means outside of said predetermined operating range to establish a second signal from said first sensor, a second sensor, means coupled to said second sensor and responsive to movement of said feed tube into said first position for establishing a third signal from said second sensor, an OR-gate, and means for applying said signals to said motor through said OR-gate to energize said motor in response to signals from said first sensor and said second sensor.

12. Apparatus according to claim 11 wherein said moving means includes a servomotor having a shaft and a pivot arm carrying said sample feed tube carried by said shaft, first and second stops, said shaft being movable between said stops and determining the first and the second positions of said feed tube, said first stop comprising a switch contact and forming part of said second sensor.

13. Apparatus according to claim 12 wherein said second sensor includes a contact pin carried by said shaft and electrically connected to ground, a source of voltage, a resistor, said first stop being insulated and connected through said resistor to said voltage source, and an inverter having an input terminal connected to said stop and an output representative of said third signal of said second sensor.

* * * * *